US010076718B2

(12) United States Patent
Hidaka et al.

(10) Patent No.: US 10,076,718 B2
(45) Date of Patent: Sep. 18, 2018

(54) FILTERING MEDIUM FOR DEODORIZING FILTER

(71) Applicant: TOYOBO CO., LTD., Osaka-shi, Osaka (JP)

(72) Inventors: Yusuke Hidaka, Otsu-Shi (JP); Sadahito Goto, Otsu-Shi (JP)

(73) Assignee: TOYOBO CO., LTD., Osaka-shi (JP)

( * ) Notice: Subject to any disclaimer, the term of this patent is extended or adjusted under 35 U.S.C. 154(b) by 0 days.

(21) Appl. No.: 14/896,256

(22) PCT Filed: Jun. 4, 2014

(86) PCT No.: PCT/JP2014/064838

§ 371 (c)(1),
(2) Date: Dec. 4, 2015

(87) PCT Pub. No.: WO2014/196564

PCT Pub. Date: Dec. 11, 2014

(65) Prior Publication Data

US 2016/0175753 A1 Jun. 23, 2016

(30) Foreign Application Priority Data

Jun. 7, 2013 (JP) ................................ 2013-120617
Jul. 31, 2013 (JP) ................................ 2013-159570

(51) Int. Cl.

| | |
|---|---|
| ***B01D 53/02*** | (2006.01) |
| ***B01D 46/00*** | (2006.01) |
| ***B03C 3/28*** | (2006.01) |
| ***B01D 39/16*** | (2006.01) |
| ***A61L 9/16*** | (2006.01) |

(52) U.S. Cl.

CPC ............ *B01D 46/0038* (2013.01); *A61L 9/16* (2013.01); *B01D 39/163* (2013.01); *B01D 46/0036* (2013.01); *B03C 3/28* (2013.01); *B01D 2239/045* (2013.01); *B01D 2239/0435* (2013.01); *B01D 2239/0659* (2013.01)

(58) Field of Classification Search

CPC .............. A61L 9/16; B01D 2239/0435; B01D 2239/045; B01D 2239/0659; B01D 39/163; B01D 46/0036; B01D 46/0038; B03C 3/28

See application file for complete search history.

(56) References Cited

U.S. PATENT DOCUMENTS

| | | | |
|---|---|---|---|
| 5,792,513 A | 8/1998 | Koslow et al. | |
| 6,077,588 A | 6/2000 | Koslow et al. | |
| 6,355,330 B1 | 3/2002 | Koslow et al. | |
| 6,485,813 B1 | 11/2002 | Koslow | |
| 2003/0207635 A1 | 11/2003 | Minemura et al. | |
| 2008/0047430 A1 | 2/2008 | Kobori | |
| 2008/0153375 A1* | 6/2008 | Wilfong .................. | D04H 1/54 442/415 |

FOREIGN PATENT DOCUMENTS

| | | |
|---|---|---|
| JP | 11-5058 A | 1/1999 |
| JP | 11-156124 A | 6/1999 |
| JP | 11-221412 A | 8/1999 |
| JP | 2000-117024 A | 4/2000 |
| JP | 2002-273123 A | 9/2002 |
| JP | 2002-292227 A | 10/2002 |
| JP | 2003-275517 A | 9/2003 |
| JP | 2007-38091 A | 2/2007 |
| JP | 2007-301434 A | 11/2007 |
| JP | 2008-043885 A | 2/2008 |
| JP | 2008-104557 A | 5/2008 |

OTHER PUBLICATIONS

International Search Report dated Sep. 16, 2014, issued in counterpart Application No. PCT/JP2014/064838 (2 pages).
Office Action dated Sep. 23, 2016, issued in counterpart Chinese Application No. 201480032548.2, with English translation. (16 pages).
Office Action dated Apr. 17, 2017, issued in counterpart Chinese Application No. 201480032548.2, with English translation. (13 pages).
Extended (supplementary) European Search Report dated Jan. 25, 2017, issued in counterpart European Application No. 14806870.3. (6 pages).
Office Action dated Sep. 26, 2017, issued in counterpart Japanese Application No. 2014-115615, with English translation (6 pages).
Office Action dated Oct. 24, 2017, issued in counterpart Japanese Application No. 2014-115616, with English translation (6 pages).

* cited by examiner

*Primary Examiner* — Christopher P Jones
(74) *Attorney, Agent, or Firm* — Westerman, Hattori, Daniels & Adrian, LLP

(57) ABSTRACT

It is provided that a filtering medium for deodorizing filter which can sufficiently exhibit deodorizing capability and are excellent in pressure loss and dust-holding capacity while improving adhesion and rigidity. A filtering medium for deodorizing filter having a laminated structure formed by sandwiching an adsorbing layer containing an adsorbent and an adhesive between base material layers, wherein at least one layer of the base material layers is a laminate sheet obtained by integrally laminating a nonwoven fabric made of thermal-bonding-based long fibers and a needle-punched electret nonwoven fabric by needle punching; and the adsorbing layer and the nonwoven fabric made of thermal-bonding-based long fibers of the laminate sheet are laminated so as to be adjacent to each other and thermally bonded to each other.

4 Claims, No Drawings

FILTERING MEDIUM FOR DEODORIZING FILTER

TECHNICAL FIELD

The present invention relates to a filtering medium for deodorizing filter excellent in adhesion and rigidity and to a filtering medium for deodorizing filter having low pressure loss, high efficiency, and high dust-holding capacity.

BACKGROUND ART

In recent years, demands for high performance and low cost of filtering media have been increased in the field of filters for air conditioning, air conditioners, and automobiles, and many investigations on filtering media for filters which simultaneously satisfy both dust-removing capability and deodorizing capability have been made. Generally, in order to provide deodorizing capability, methods for making sheets by using granular or fibrous adsorbents and adhesives have often been employed and, for example, adsorbing filtering media have been developed which are obtained by spraying a mixture of a granular adsorbent and a granular adhesive between base materials and heat-bonding the resulting materials (e.g., Patent Document 1). However, because of weak adhesive strength, the adsorbing filtering media have problems of dropping of the adsorbent and lowering of the rigidity.

In order to solve such problems, there is a method for increasing the mixing ratio of an adhesive, but the method causes decrease in deodorizing capability due to the coating on the adsorbent surface or increase in pressure loss. Patent Document 2 discloses that a needle-punched nonwoven fabric and an adsorbing layer are adjacent, to each other and the fluff of the needle-punched nonwoven fabric enters in the adsorbing layer to increase the adhesive strength due to an anchor effect. However, in the case where the fluff of the filtering medium surface is noticeable, the appearance grade is undesirably deteriorated and the rigidity is also insufficient.

PRIOR ART DOCUMENTS

Patent Documents

Patent Document 1: JP-A-hei-11-5058
Patent Document 2: JP-A-2007-301434

SUMMARY OF THE INVENTION

Problems to be Solved by the Invention

An object of the present invention is to provide a filtering medium for deodorizing filter which can sufficiently exhibit deodorizing capability and are excellent in pressure loss, particles-collecting efficiency, and dust-holding capacity while improving adhesion and rigidity.

Solutions to the Problems

The present inventors have made various investigations and have found that the above-mentioned problems could be solved by the following means. The findings have led to the present invention. The present invention is as follows.

(1) A filtering medium for deodorizing filter having a laminated structure formed by sandwiching an adsorbing layer containing an adsorbent and an adhesive between base material layers, wherein at least one layer of the base material layers is a laminate sheet obtained by integrally laminating a nonwoven fabric made of thermal-bonding-based long fibers and a nonwoven fabric made of polyolefin-based fibers and polyester-based fibers (hereinafter referred to as mixed fiber sheet) by needle punching; and the adsorbing layer and the nonwoven fabric made of thermal-bonding-based long fibers of the laminate sheet are laminated so as to be adjacent to each other and thermally bonded to each other.

(2) A filtering medium for deodorizing filter having a laminate structure formed by sandwiching 10 to 450 $g/m^2$ of an adsorbing layer containing an adsorbent and an adhesive between base material layers, wherein at least one layer of the base material layers is a laminate sheet obtained by laminating a nonwoven fabric made of thermal-bonding-based long fibers having a weight per unit area of 5 to 40 $g/m^2$ and a melt-blown nonwoven fabric; and the adsorbing layer and the nonwoven fabric made of thermal-bonding-based long fibers of the laminate sheet are laminated so as to be adjacent to each other and thermally bonded to each other.

(3) The filtering medium for deodorizing filter according to (1) or (2), wherein the nonwoven fabric made of thermal-bonding-based long fibers is a nonwoven fabric made of composite thermal-bonding-based long fibers having a core-sheath structure.

Effect of the Invention

The present invention relates to a filtering medium for deodorizing filter excellent in adhesion and rigidity and can provide a filtering medium for deodorizing filter having low pressure loss, high efficiency, and high dust-holding capacity.

MODE FOR CARRYING OUT THE INVENTION (Embodiment 1)

Embodiment 1 of the present invention is a filtering medium having a laminated structure formed by sandwiching an adsorbing layer containing an adsorbent and an adhesive between base material layers, characterized in that at least one layer of the base material layers is a laminate sheet obtained by integrally laminating a long fiber nonwoven fabric made of thermal-bonding-based fibers and a nonwoven fabric made of polyolefin-based fibers and polyester-based fibers by needle punching; the adsorbing layer and the nonwoven fabric made of thermal-bonding-based long fibers of the laminate sheet are laminated so as to be adjacent to each other; and a low melting point component of the thermal-bonding-based long fibers constituting the nonwoven fabric made of thermal-bonding-based long fibers and the adsorbing layer are firmly bonded to each other by thermal-bonding.

In a nonwoven fabric made of thermal-bonding-based short fibers, a low melting point component of the thermal-bonding-based short fibers and the adsorbent are bonded, but the short fibers move easily also in the thickness direction and therefore, the mobility of the adsorbent is high and it results in failure to obtain sufficient rigidity as a filtering medium. In contrast, in the case of the nonwoven fabric made of thermal-bonding-based long fibers, the fibers are hard to move in the thickness direction and therefore, the mobility of the adsorbent bonded to the nonwoven fabric made of thermal-bonding-based long fibers is low and high rigidity as a filtering medium can be obtained.

It is preferable that the nonwoven fabric made of thermal-bonding-based long fibers in Embodiment 1 includes composite long fibers having a core-sheath structure as constituent fibers, and the material for the core part is polyethylene terephthalate, polybutylene terephthalate, or the like having high melting point, and the material for the sheath part is polyethylene, polypropylene, low melting point polyesters, or the like having low melting point.

If the thermal-bonding-based long fibers have a core-sheath structure, even though the sheath part is reduced due to thermal-bonding, the core component remains, and therefore, the flatness of the nonwoven fabric made of thermal-bonding-based long fibers is not deteriorated. Further, the fibers do not move in the thickness direction so that high rigidity can be maintained as a filtering medium.

The nonwoven fabric made of thermal-bonding-based long fibers in Embodiment 1 preferably has a weight per unit area of 5 to 40 $g/m^2$, and more preferably 10 to 30 $g/m^2$. If the weight per unit area is less than 5 $g/m^2$, the area thermally bonded to the adsorbing layer is small and sufficient adhesive strength cannot be obtained. On the other hand, if the weight per unit area exceeds 40 $g/m^2$, not only the pressure loss becomes large along with an increase in the number of fibers, but also the dust-holding spaces between fibers are decreased so that the dust-holding capacity is lowered.

The thermal-bonding-based long fibers constituting the nonwoven fabric made of thermal-bonding-based long fibers in Embodiment 1 preferably have a fiber diameter of 3 to 100 more preferably 5 to 80 μm, and furthermore preferably 10 to 60 μm. This is because if the fiber diameter falls within the above range, the adsorbing layer and the mixed fiber sheet fabric are anchored while flexibility is maintained, and the adhesive strength and the rigidity can be sufficiently improved.

Use of a mixed fiber sheet is indispensable for the filtering medium for deodorizing filter in Embodiment 1. This is because the demand for high performance in filtering medium has been increasing and a filtering medium is required to have both properties, the deodorizing capability and fine dust- removal capability. The materials are not particularly limited, and those usable for the polyolefin-based fibers are polyethylene, polypropylene, and the like; and those usable for the polyester-based fibers are polyethylene terephthalate, polytrimethylene terephthalate, aromatic polyesters, and the like.

The polyolefin-based fibers and the polyester-based fibers constituting the mixed fiber sheet fabric in Embodiment 1 preferably have a fiber diameter of 3 to 30 μm. This is because if the fiber diameter falls within the above range, the pressure loss is low and fine dust can be removed sufficiently. The mixing ratio of the polyolefin-based fibers and the polyester-based fibers is preferably 30:70 to 70:30 by mass. This is because if the mixing ratio falls within the above range, charging can be effectively caused.

The cross-sectional shape of the fibers constituting the mixed fiber sheet in Embodiment 1 is not particularly limited and may be any of circular shape, triangular shape, rectangular shape and irregular shape, but fibers with a circular cross-sectional shape are preferable. This is because if the fibers have, for example, a rectangular cross-sectional shape, the contact area among the fibers is increased so that it causes a decrease in an effective fiber surface area. If the cross-sectional shape of the fibers is not a shape having no straight line part, not only a perfect circular shape but also an elliptical shape can be accepted. Further, the length of the fibers is preferably 10 to 100 mm, and more preferably 30 to 80 mm, although depending on the means for making a sheet of a mixed fiber sheet. This is because if the length falls within the above range, more uniform webs can be produced in carding of the fibers.

The mixed fiber sheet in Embodiment 1 preferably has a weight per unit area of 10 to 100 $g/m^2$, and more preferably 10 to 50 $g/m^2$. If the weight per unit area is less than 10 $g/m^2$, fine dust cannot be removed sufficiently. If the weight per unit area exceeds 100 $g/m^2$, the pressure loss is increased so that it is not preferable in use of filters.

The nonwoven fabric made of thermal-bonding-based long fibers and the needle-punched electret nonwoven fabric in Embodiment 1 are laminated by needle punching. This is because ifthe nonwoven fabric and the mixed fiber sheet are integrally laminated by needle punching, the fibers constituting the needle-punched electret nonwoven fabric can be strongly interlaced with the nonwoven fabric made of thermal-bonding-based long fibers in the thickness direction, and the penetrating fibers can be bonded to the adsorbing layer to secondarily increase the adhesive strength.

Examples of the shape of the adsorbent in Embodiment 1 include a powder shape, a granular shape, a crushed shape, a granulated shape and a beads shape, but activated carbon-based which can adsorb a wide variety of gases is preferable. For example, coconut husk-based, wood-based, petroleum-based, and pitch-based activated carbons are preferable. The number of pores for introduction into the inside, so-called macropores, observed by surface observation is preferably large. This is because when a particulate mixture of activated carbon and a thermoplastic powder resin is produced, even if the thermoplastic powder resin covers the surface of the activated carbon, fine pores with absorbing capability can be opened due to gas desorption from the fine pore insides at the time of thermal pressing process. As the surface of the activated carbon is rougher to a certain extent, the fluidity of the melted resin is worsened and deterioration in adsorbing capability can be suppressed.

In consideration of air permeability, dropping of the adsorbing material, sheet processability and the like, the adsorbent in Embodiment 1 preferably has a particle size range of 60 to 1000 μm, and more preferably 100 to 900 μm based on the value according to the JIS standard sieving (JIS Z8801). If the particle size range is less than 60 μm, the pressure loss becomes too large for obtaining a certainly high adsorbing capacity and the filling density of the sheet is high so that the pressure loss is rapidly increased at the time of dust load and the dust-holding capacity is lowered. If the particle size range exceeds 1000 μm, dropping of the adsorbing material from the sheet tends to occur easily, the initial adsorbing capability by one-pass is extremely lowered, and moreover the processability at the time of folding and corrugation is lowered when a pleated or corrugated filter unit for air purification is produced. The above-mentioned powdery or particulate adsorbent can be obtained by adjusting the particle size to a predetermined size with the use of a common sieving apparatus.

The amount of the adsorbent to be sandwiched between the base material layers of the filtering medium in Embodiment 1 is preferably 10 to 450 $g/m^2$, and more preferably 50 to 350 $g/m^2$. If is the amount falls within the above range, sufficient deodorizing capability can be obtained while the considerable increase of the pressure loss is suppressed.

The adsorbent to be used for the filtering medium for deodorizing filter in Embodiment 1 may be subjected to chemical treatment for the purpose of improving the adsorbing capability for polar substances and aldehydes. As the chemicals to be used for gas chemical treatment, the followings are preferably used: for example, amine-based agents such as ethanolamine, polyethyleneimine, aniline, p-anisidine and sulfanilic acid, as well as sodium hydroxide, potassium hydroxide, guanidine carbonate, guanidine phosphate, aminoguanidine sulfate, 5,5-dimethylhydantoin, benzoguanamine, 2,2-iminodiethanol, 2,2,2-nitrotriethanol, ethanolamine hydrochloride, 2-aminoethanol, 2,2-iminodiethanol hydrochloride, p-aminobenzoic acid, sodium sulfanilate, L-arginine, methylamine hydrochloride, semicarbazide hydrochloride, hydrazine, hydroquinone, hydroxylamine sulfate, permanganate, potassium carbonate, potassium hydrogen carbonate, etc., for acidic polar substances like aldehyde-based gases, nitrogen compounds such as NOx, sulfur compounds such as SOx, and acetic acid; and for example, phosphoric acid, citric acid, malic acid, ascorbic acid, tartaric acid, etc., for basic polar substances such as ammonia, methylamine, trimethylamine and pyridine. These adsorbents subjected to chemical treatment may be used alone or may be used by mixing with an adsorbent without being subjected to chemical treatment. The chemical treatment can be performed by, for example, carrying a chemical on the adsorbent or loading a chemical to the adsorbent. Other than a direct treatment of the adsorbent with a chemical, it is also possible to employ a method for loading and processing of a chemical near the sheet surface by common coating method or a method for impregnation and loading of a chemical in the entire sheet. In this case, the following method can be performed: a method for producing an aqueous chemical solution mixed with thickener such as sodium alginate or polyethylene oxide, followed by carrying and loading of the solution. This method is effective for carrying and loading of a chemical having low solubility in water and further for suppression of dropping the chemical.

The adhesive to be used in Embodiment 1 is preferably a thermoplastic powder resin. If the adhesive is a powder resin, the adhesive can be uniformly dispersed to an adsorbent and the fluff and low melting point parts of a laminate sheet obtained by integrally laminating the nonwoven fabric made of thermal-bonding-based long fibers and the mixed fiber sheet. Examples of the kinds of the thermoplastic powder resin include polyolefin-based resins, polyamide-based resins, polyester-based resins and ethylene-acryl copolymer resins.

The thermoplastic powder resin to be used as the adhesive in Embodiment 1 preferably has a particle size of 1 to 40 μm, and more preferably 5 to 30 μm as an average particle size. It is further preferable that 95 wt % or more of the thermoplastic powder resin has a particle size within a range of 1 to 40 μm. This is because if the powder resin has the above average particle size, clogging of the surface fine pores of the particulate adsorbent with the thermoplastic resin can be reduced, and further, preliminary adhesion to the particulate adsorbent due to Van der Walls force or electrostatic force is efficiently performed at the time of mixing with the adsorbent and the powder resin can be uniformly dispersed and partial separation between the adsorbent layer and the base material layer can be effectively prevented.

The shape of the thermoplastic powder resin to be used as the adhesive in Embodiment 1 is not particularly limited, examples thereof include a spherical shape and a crushed shape. Naturally, two or more kinds of thermoplastic powder resins may be used in combination. Even in the case of using a particulate adsorbent carrying a chemical or a base material nonwoven fabric carrying a chemical, when the thermoplastic powder resin is used, the thermoplastic powder resin is in the state of temporarily bonding to the surface of the particulate adsorbent from the time of mixing in a dry state. Thus, mutual interference can be avoided in the subsequent sheet making step even if the chemicals have different characteristics so that a sufficient effect can be exhibited.

The thermoplastic powder resin to be contained in the filtering medium for deodorizing filter in Embodiment 1 is used in an amount of preferably 1 to 40 wt %, and more preferably 3 to 30 wt % to the particulate adsorbent. This is because if the amount falls within the above range, it is possible to obtain a filtering medium for deodorizing filter excellent in adhesive force to the base material layers, pressure loss, and deodorizing capability.

The filtering medium for deodorizing filter in Embodiment 1 may be configured with inclusion of components, etc., having collateral functions such as an antibacterial agent, an antifungal agent, an antiviral agent and a flame retardant. These components may be kneaded in fibers or nonwoven fabrics, or may be provided by loading or carrying these components in the subsequent process. For example, it is possible to produce a filtering medium for deodorizing filter satisfying the flame retardation standard defined in FMVSS.302 or UL flame retardant regulation by configuring the filtering medium with inclusion of a flame retardant.

When a sheet is produced by finally thermally-pressing the filtering medium for deodorizing filter in Embodiment 1, a hot roll press method which is often used or a flat bed lamination method performed by sandwiching the filtering medium between both upper and lower flat heat belt conveyers is available. The latter method is more preferable for making more uniform thickness and adhesion state. The combination of the laminate sheet for base material layers and the characteristics of the above-mentioned production method described in this patent application can suppress excess bonding of the particulate adsorbents to each other and at the same time can give adhesive strength sufficient for practical use with the laminate sheet for base material layers.

A method for producing the filtering medium for deodorizing filter in Embodiment 1 will be described. First, predetermined weights of an adsorbent and an adhesive are weighed, put in a stirrer, and stirred at a rotation speed of 30 rpm for about 10 minutes. Next, the resulting mixed powder is sprayed to the side of a nonwoven fabric made of thermal-bonding-based long fibers of a laminate sheet, further a base material layer is superposed thereon and the resulting product is subjected to thermal press treatment. The temperature of the sheet surface at the time of thermal pressing is higher than the melting point of the thermoplastic resin by 3 to 30° C., and preferably 5 to 20° C.

The filtering medium for deodorizing filter in Embodiment 1 preferably has a thickness of 0.1 to 3.0 mm, and more preferably 0.5 to 2.0 mm. If the thickness is less than 0.1 mm, the dust collecting space is small so that the pressure loss at the time of dust load is rapidly increased, and clogging occurs. If the thickness exceeds 3.0 mm, the thickness of the entire sheet is too thick so that the structure resistance becomes large when the filtering medium is formed into a pleated unit, and as a result, the pressure loss of the entire unit is increased too much and therefore the filtering medium is problematic in terms of practical use.

The filtering medium for deodorizing filter in Embodiment 1 preferably has a weight per unit area of 30 to 500 $g/m^2$. If the weight per unit area is less than 30 $g/m^2$, the rigidity of the filtering medium is weak so that the unit is deformed at the time of ventilation load and the pressure loss is increased. If the weight per unit area exceeds 500 $g/m^2$, the thickness of the sheet is large so that the structure resistance becomes large when the filtering medium is formed into a pleated unit, and the filtering medium is problematic in terms of practical use.

A pleated filter unit obtained by using the filtering medium for deodorizing filter in Embodiment 1 preferably has a thickness of 10 to 400 mm. In the case of an air purification apparatus for vehicles including a built-in type automotive air conditioner or for domestic use, the thickness is about 10 to 60 mm in relation to a common inner space, and in the case of a large scale filter unit to be often installed for air conditioning in buildings, the thickness is preferably 40 to 400 mm in consideration of housing space.

(Embodiment 2)

Embodiment 2 of the present invention is a filtering medium for deodorizing filter having a laminated structure formed by sandwiching an adsorbing layer containing an adsorbent and an adhesive between base material layers, characterized in that at least one layer of the base material layers is a laminate sheet obtained by laminating a nonwoven fabric made of thermal-bonding-based long fibers and a melt-blown nonwoven fabric; the adsorbing layer and the nonwoven fabric made of thermal-bonding-based long fibers of the laminate sheet are laminated so as to be adjacent to each other; and a low melting point component of the nonwoven fabric made of thermal-bonding-based long fibers and the adsorbing layer are firmly bonded to each other by thermal-bonding.

In a nonwoven fabric made of thermal-bonding-based short fibers, a low melting point component of the thermal-bonding-based short fibers and the adsorbent are bonded, but the short fibers move easily also in the thickness direction and therefore, the mobility of the adsorbent is high and it results in failure to obtain sufficient rigidity as a filtering medium. In contrast, in the case of the nonwoven fabric made of thermal-bonding-based long fibers, the fibers are hard to move in the thickness direction and therefore, the mobility of theadsorbent bonded to the nonwoven fabric made of thermal- bonding-based long fibers is low and high rigidity as a filtering medium can be obtained.

It is preferable that the nonwoven fabric made of thermal-bonding-based long fibers in Embodiment 2 includes composite long fibers having a core-sheath structure as constituent fibers, and the material for the core part is polyethylene terephthalate, polybutylene terephthalate, or the like having high melting point, and the material for the sheath part is polyethylene, polypropylene, low melting point polyesters, or the like having low melting point.

If the thermal-bonding-based long fibers have a core-sheath structure, even though the sheath part is reduced due to thermal-bonding, the core component remains, and therefore, the flatness of the nonwoven fabric made of thermal-bonding-based long fibers is not deteriorated. Further, the fibers do not move in the thickness direction so that high rigidity can be maintained as a filtering medium.

The nonwoven fabric made of thermal-bonding-based long fibers in Embodiment 2 has a weight per unit area of 5 to 40 g/m$^2$, and preferably 10 to 30 g/m$^2$. If the weight per unit area is less than 5 g/m$^2$, the area thermally bonded to the adsorbing layer is small and sufficient adhesive strength cannot be obtained. On the other hand, if the weight per unit area exceeds 40 g/m$^2$, not only the pressure loss becomes large along with an increase in the number of fibers, but also the dust-holding spaces between fibers are decreased so that the dust-holding capacity is lowered.

The thermal-bonding-based long fibers constituting the nonwoven fabric made of thermal-bonding-based long fibers in Embodiment 2 preferably have a fiber diameter of 3 to 100 μm, more preferably 5 to 80 μm, and furthermore preferably 10 to 60 μm. This is because if the fiber diameter falls within the above range, the adsorbing layer and the melt-blown nonwoven fabric are anchored while flexibility is maintained, and the adhesive strength and the rigidity can be sufficiently improved.

The melt-blown nonwoven fabric in Embodiment 2 is not particularly limited, and examples of the raw material for the melt-blown nonwoven fabric include resins such as polyolefin, polyester, polylactic acid, polycarbonate, polyvinyl chloride and polyvinylidene chloride, and among them, polypropylene is preferable.

The melt-blown nonwoven fabric in Embodiment 2 preferably has a weight per unit area of 5 to 100 g/m$^2$, and more preferably 10 to 60 g/m$^2$. If the weight per unit area is less than 5 g/m$^2$, the number of the fibers is low so that high collection efficiency cannot be obtained. On the other hand, if the weight per unit area exceeds 100 g/m$^2$, the pressure loss becomes large.

The fibers constituting the melt-blown nonwoven fabric in Embodiment 2 preferably have a fiber diameter of 1 to 20 μm, and more preferably 1 to 10 μm. If the fiber diameter is less than 1 μm, not only the pressure loss is increased but also the pressure loss at the time of dust load is rapidly increased so that the useful lifetime of the filter is shortened. If the fiber diameter exceeds 20 μm, high collection efficiency cannot be obtained.

A method for laminating the nonwoven fabric made of thermal-bonding-based long fibers and the melt-blown nonwoven fabric is not particularly limited, but preferable is a method for heating at a temperature equal to or higher than the melting point of low melting point components of the long fibers constituting the nonwoven fabric made of thermal-bonding-based long fibers. An example of the heating method includes a method of simultaneously inserting the melt-blown nonwoven fabric and the nonwoven fabric made of thermal-bonding-based long fibers between two heat rolls and performing heat pressing by adjusting the gap between the two rolls.

Besides, a method of spraying an adhesive resin or a method of using needle punching may also be employed.

Examples of the shape of the adsorbent in Embodiment 2 include a powder shape, a granular shape, a crushed shape, a granulated shape and a beads shape, but activated carbon-based which can adsorb a wide variety of gases is preferable. For example, coconut husk-based, wood-based, petroleum-based, and pitch-based activated carbons are preferable. The number of pores for introduction into the inside, so-called macropores, observed by surface observation is preferably large. This is because when a particulate mixture of activated carbon and a thermoplastic powder resin is produced, even if the thermoplastic powder resin covers the surface of the activated carbon, fine pores with absorbing capability can be opened due to gas desorption from the fine pore insides at the time of thermal pressing process. As the surface of the activated carbon is rougher to a certain extent, the fluidity of the melted resin is worsened and deterioration in adsorbing capability can be suppressed.

In consideration of air permeability, dropping of the adsorbing material, sheet processability and the like, the adsorbent in Embodiment 2 preferably has a particle size range of 60 to 1000 μm, and more preferably 100 to 900 μm based on the value according to the JIS standard sieving (JIS Z8801). If the particle size range is less than 60 μm, the pressure loss becomes too large for obtaining a certainly high adsorbing capacity and the filling density of the sheet is high so that the pressure loss is rapidly increased at the time of dust load and the dust-holding capacity is lowered. If the particle size range exceeds 1000 μm, dropping of the adsorbing material from the sheet tends to occur easily, the initial adsorbing capability by one-pass is extremely lowered, and moreover the processability at the time of folding and corrugation is lowered when a pleated or corrugated filter unit for air purification is produced. The above-mentioned powdery or particulate adsorbent can be obtained by adjusting the particle size to a predetermined size with the use of a common sieving apparatus.

The amount, of the adsorbent to be sandwiched between the base material layers of the filtering medium in Embodiment 2 is preferably 10 to 450 $g/m^2$, and more preferably 50 to 350 $g/m^2$. If is the amount falls within the above range, sufficient deodorizing capability can be obtained while the considerable increase of the pressure loss is suppressed.

The adsorbent to be used for the filtering medium for deodorizing filter in Embodiment 2 may be subjected to chemical treatment for the purpose of improving the adsorbing capability for polar substances and aldehydes. As the chemicals to be used for gas chemical treatment, the followings are preferably used: for example, amine-based agents such as ethanolamine, polyethyleneimine, aniline, p-anisidine and sulfanilic acid, as well as sodium hydroxide, potassium hydroxide, guanidine carbonate, guanidine phosphate, aminoguanidine sulfate, 5,5-dimethylhydantoin, benzoguanamine, 2,2-iminodiethanol, 2,2,2-nitrotriethanol, ethanolamine hydrochloride, 2-aminoethanol, 2,2-iminodiethanol hydrochloride, p-aminobenzoic acid, sodium sulfanilate, L-arginine, methylamine hydrochloride, semicarbazide hydrochloride, hydrazine, hydroquinone, hydroxylamine sulfate, permanganate, potassium carbonate, potassium hydrogen carbonate, etc., for acidic polar substances like aldehyde-based gases, nitrogen compounds such as NOx, sulfur compounds such as SOx, and acetic acid; and for example, phosphoric acid, citric acid, malic acid, ascorbic acid, tartaric acid, etc., for basic polar substances such as ammonia, methylamine, trimethylamine and pyridine. These adsorbents subjected to chemical treatment may be used alone or may be used by mixing with an adsorbent without being subjected to chemical treatment. The chemical treatment can be performed by, for example, carrying a chemical on the adsorbent or loading a chemical to the adsorbent. Other than a direct treatment of the adsorbent with a chemical, it is also possible to employ a method for loading and processing of a chemical near the sheet surface by common coating method or a method for impregnation and loading of a chemical in the entire sheet. In this case, the following method can be performed: a method for producing an aqueous chemical solution mixed with thickener such as sodium alginate or polyethylene oxide, followed by carrying and loading of the solution. This method is effective for carrying and loading of a chemical having low solubility in water and further for suppression of dropping the chemical.

The adhesive to be used in Embodiment 2 is preferably a thermoplastic powder resin. If the adhesive is a powder resin, the adhesive can be uniformly dispersed to an adsorbent and the fluff and low melting point parts of a laminate sheet. Examples of the kinds of the thermoplastic powder resin include polyolefin-based resins, polyamide-based resins, polyester-based resins and ethylene-acryl copolymer resins.

The thermoplastic powder resin to be used as the adhesive in Embodiment 2 preferably has a particle size of 1 to 40 μm, and more preferably 5 to 30 μm as an average. It is further preferable that 95 wt % or more of the thermoplastic powder resin has a particle size within a range of 1 to 40 μm. This is because if the powder resin has the above particle size, clogging of the surface fine e pores of the particulate adsorbent with the thermoplastic resin can be reduced, and further, preliminary adhesion to the particulate adsorbent due to Van der Walls force or electrostatic force is efficiently performed at the time of mixing with the adsorbent and the powder resin can be uniformly dispersed and partial separation between the adsorbent layer and the base material layer can be effectively prevented.

The shape of the thermoplastic powder resin to be used as the adhesive in Embodiment 2 is not particularly limited, examples thereof include a spherical shape and a crushed shape. Naturally, two or more kinds of thermoplastic powder resins may be used in combination. Even in the case of using a particulate adsorbent carrying a chemical or a base material nonwoven fabric carrying a chemical, when the thermoplastic powder resin is used, the thermoplastic powder resin is in the state of temporarily bonding to the surface of the particulate adsorbent from the time of mixing in a dry state. Thus, mutual interference can be avoided in the subsequent sheet making step even if the chemicals have different characteristics so that a sufficient effect can be exhibited.

The thermoplastic powder resin to be contained in the filtering medium for deodorizing filter in Embodiment 2 is used in an amount of preferably 1 to 40 wt %, and more preferably 3 to 30 wt % to the particulate adsorbent. This is because if the amount falls within the above range, it is possible to obtain a filtering medium for deodorizing filter excellent in adhesive force to the base material layers, pressure loss, and deodorizing capability.

The filtering medium for deodorizing filter in Embodiment 2 may be configured with inclusion of components, etc., having collateral functions such as an antibacterial agent, an antifungal agent, an antiviral agent and a flame retardant. These components may be kneaded in fibers or nonwoven fabrics, or may be provided by loading or carrying these components in the subsequent process. For example, it is possible to produce a filtering medium for deodorizing filter satisfying the flame retardation standard defined in FMVSS.302 or UL flame retardant regulation by configuring the filtering medium with inclusion of a flame retardant.

When a sheet is produced by finally thermally-pressing the filtering medium for deodorizing filter in Embodiment 2, a hot roll press method which is often used or a flat bed lamination method performed by sandwiching the filtering medium between both upper and lower flat heat belt conveyers is available. The latter method is more preferable for making more uniform thickness and adhesion state. The combination of the base material nonwoven fabric and the characteristics of the above-mentioned production method described in this patent application can suppress excess bonding of the particulate adsorbents to each other and at the same time can give adhesive strength sufficient for practical use with the base material nonwoven fabric.

A method for producing the filtering medium for deodorizing filter in Embodiment 2 will be described. First, predetermined weights of an adsorbent and an adhesive are weighed, put in a stirrer, and stirred at a rotation speed of 30 rpm for about 10 minutes. Next, the resulting mixed powder is sprayed to the side of the nonwoven fabric made of thermal-bonding-based long fibers in the laminate sheet obtained by laminating the nonwoven fabric made of thermal-bonding-based long fibers and the melt-blown nonwoven fabric, and further a base material layer is superposed thereon and the resulting product is subjected to thermal press treatment. The temperature of the sheet surface at the time of thermal pressing is higher than the melting point of the thermoplastic resin by 3 to 30° C., and preferably 5 to 20° C. The base material layer to be superposed on the adsorbing layer containing the adsorbent and the adhesive is not particularly limited, but it is preferable to use a thermally bonded nonwoven fabric.

The filtering medium for deodorizing filter in Embodiment 2 preferably has a thickness of 0.1 to 3.0 mm, and more preferably 0.5 to 2.0 mm. If the thickness is less than 0.1 mm, the dust collecting space is small so that the pressure loss at the time of dust load is rapidly increased, and clogging occurs. If the thickness exceeds 3.0 mm, the thickness of the entire sheet is too thick so that the structure resistance becomes large when the filtering medium is formed into a pleated unit, and as a result, the pressure loss of the entire unit is increased too much and therefore the filtering medium is problematic in terms of practical use.

The filtering medium for deodorizing filter in Embodiment 2 preferably has a weight per unit area of 30 to 500 $g/m^2$. If the weight per unit area is less than 30 $g/m^2$, the rigidity of the filtering medium is weak so that the unit is deformed at the time of ventilation load and the pressure loss is increased. If the weight per unit area exceeds 500 $g/m^2$, the thickness of the sheet is large so that the structure resistance becomes large when the filtering medium is formed into a pleated unit, and the filtering medium is problematic in terms of practical use.

A pleated filter unit obtained by using the filtering medium for deodorizing filter in Embodiment 2 preferably has a thickness of 10 to 400 mm. In the case of an air purification apparatus for vehicles including a built-in type automotive air conditioner or for domestic use, the thickness is about 10 to 60 mm in relation to a common inner space, and in the case of a large scale filter unit to be often installed for air conditioning in buildings, the thickness is preferably 40 to 400 mm in consideration of housing space.

EXAMPLES

Hereinafter, the present invention will be more specifically described with reference to Examples below. The properties shown in Examples were measured by the following methods.

(Pressure Loss of Filtering Medium)

A filtering medium was set in a duct and atmospheric air ventilation was performed in such a manner that the air filtration speed was adjusted to 31 cm/s. The static pressure difference between the upstream and the downstream of the filtering medium was read with a differential pressure gauge to measure the pressure loss (Pa).

(Collection Efficiency for 0.3 μm Particles)

A filtering medium was set in a duct and atmospheric air ventilation was performed in such a manner that the air filtration speed was adjusted to 16 cm/s. The concentration by number of 0.3 to 0.5 μm particles in the upstream and downstream of the filtering medium was measured by a particle counter and the particle collection efficiency was calculated according to the following equation.

$$\text{Particle collection efficiency (\%)} = [1 - (\text{concentration in downstream side}/\text{concentration in upstream side})] \times 100$$

(Adhesive Strength)

The average separation strength between the base material layers in the upstream side and the downstream side was measured. The size of a specimen was 50 mm in width and 200 mm in length, and the measurement was performed at a tensile strength of 100 mm/min.

(Rigidity)

The bending resistance in the MD direction was measured according to JIS L-1096A method (Gurley method).

(Toluene Removal Efficiency)

A filtering medium was set in a duct and atmospheric air ventilation was performed in such a manner that the air filtration speed was adjusted to 16 cm/s, and toluene gas was injected in such a manner that the concentration was adjusted to 80 ppm in the upstream side of the filtering medium. The concentration in the upstream side and that of the downstream side were measured one minute after starting measurement with a hydrocarbon analyzer, and the initial removal efficiency of the toluene gas was calculated according to the following equation.

$$\text{Toluene removal efficiency (\%)} = [1 - (\text{concentration in downstream side}/\text{concentration in upstream side})] \times 100$$

(Pressure Loss of Filter)

A filter was set in a duct and atmospheric air ventilation was performed in such a manner that the air filtration speed was adjusted to 31 cm/s, and the static pressure difference between the upstream and the downstream of the filter was read with a differential pressure gauge to measure the pressure loss (Pa).

(ASHRAE Dust-Holding Capacity)

A filter was set in a duct and atmospheric air ventilation was performed in such a manner that the air filtration speed was adjusted to 31 cm/s, and ASHRAE dust was loaded in a concentration of 1.0 $g/m^3$ from the upstream side of the filter and the dust was loaded until the pressure loss became 200 Pa. The holding capacity of the dust loaded during the test was measured as the dust-holding capacity (g/filter).

Example 1-1

Polypropylene fibers (2.2 dtex, 51 mm) and polyester fibers (1.7 dtex, 44 mm) were mixed at a weight ratio of 1:1 and subjected to carding to produce mixed fiber webs having a weight per unit area of 25 $g/m^2$, and thereafter, the webs were interlaced by continuously spraying high pressure water at 3 MPa and dried to produce a mixed fiber sheet. A nonwoven fabric having a weight per unit area of 12 $g/m^2$, which was made of core-sheath type composite thermal-bonding-based long fibers (fiber diameter of 30 μm) constituted with polyester (core)/polyethylene (sheath) was integrally laminated with the mixed fiber sheet by needle punching, and further the resulting product was subjected to frictionally charging treatment to obtain an electret laminate sheet.

A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.1 was sprayed to the side of the nonwoven fabric made of thermal-bonding-based long fibers of the obtained electret laminate sheet in such a manner that the weight per unit area was 220 $g/m^2$. Further, a thermally bonded nonwoven fabric having a weight per unit area of 77 $g/m^2$ was superposed thereon as a base material layer, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 1.

Example 1-2

Polypropylene fibers (2.2 dtex, 51 mm) and polyester fibers (1.7 dtex, 44 mm) were mixed at a weight ratio of 1:1 and subjected to carding to produce mixed fiber webs having a weight per unit area of 25 g/m$^2$, and thereafter, the webs were interlaced by continuously spraying high pressure water at 3 MPa and dried to produce a mixed fiber sheet. A nonwoven fabric having a weight per unit area of 12 g/m$^2$, which was made of core-sheath type composite thermal-bonding-based long fibers (fiber diameter of 30 μm) constituted with polyester (core)/polyethylene (sheath) was integrally laminated with the mixed fiber sheet by needle punching, and further the resulting product was subjected to frictionally charging treatment to obtain an electret laminate sheet.

A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained electret laminate sheet in such a manner that the weight per unit area was 210 g/m$^2$. Further, a thermally bonded nonwoven fabric having a weight per unit area of 77 g/m$^2$ was superposed thereon as a base material layer, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 1.

Example 1-3

Polypropylene fibers (2.2 dtex, 51 mm) and polyester fibers (1.7 dtex, 44 mm) were mixed at a weight ratio of 1:1 and subjected to carding to produce mixed fiber webs having a weight per unit area of 15 g/m$^2$, and thereafter, the webs were interlaced by continuously spraying high pressure water at 3 MPa and dried to produce a mixed fiber sheet. A nonwoven fabric having a weight per unit area of 12 g/m$^2$, which was made of core-sheath type composite thermal-bonding-based long fibers (fiber diameter of 30 μm) constituted with polyester (core)polyethylene (sheath) was integrally laminated with the mixed fiber sheet by needle punching, and further the resulting product was subjected to frictionally charging treatment to obtain an electret laminate sheet.

A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained electret laminate sheet in such a manner that the weight per unit area was 315 g/m$^2$. Further, a thermally bonded nonwoven fabric having a weight per unit area of 77 g/m$^2$ was superposed thereon as a base material layer, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 1.

Example 1-4

Polypropylene fibers (2.2 dtex, 51 mm) and polyester fibers (1.7 dtex, 44 mm) were mixed at a weight ratio of 1:1 and subjected to carding to produce mixed fiber webs having a weight per unit area of 45 g/m$^2$, and thereafter, the webs were interlaced by continuously spraying high pressure water at 3 MPa and dried to produce a mixed fiber sheet. A nonwoven fabric having a weight per unit area of 20 g/m$^2$, which was made of core-sheath type composite thermal-bonding-based long fibers (fiber diameter of 30 μm) constituted with polyester (core)/polyethylene (sheath) was integrally laminated with the mixed fiber sheet by needle punching, and further the resulting product was subjected to frictionally charging treatment to obtain an electret laminate sheet.

A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained electret laminate sheet in such a manner that the weight per unit area was 315 g/m$^2$. Further, a thermally bonded nonwoven fabric having a weight per unit area of 77 g/m$^2$ was superposed thereon as a base material layer, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 1.

Example 1-5

Polypropylene fibers (2.2 dtex, 51 mm) and polyester fibers (1.7 dtex, 44 mm) were mixed at a weight ratio of 1:1 and subjected to carding to produce mixed fiber webs having a weight per unit area of 45 g/m$^2$, and thereafter, the webs were interlaced by continuously spraying high pressure water at 3 MPa and dried to produce a mixed fiber sheet. A nonwoven fabric having a weight per unit area of 12 g/m$^2$, which was made of core-sheath type composite thermal-bonding-based long fibers (fiber diameter of 30 μm) constituted with polyester (core)/polyethylene (sheath) was integrally laminated with the mixed fiber sheet by needle punching, and further the resulting product was subjected to frictionally charging treatment to obtain an electret laminate sheet.

A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained electret laminate sheet in such a manner that the weight per unit area was 315 g/m$^2$. Further, a thermally bonded nonwoven fabric having a weight per unit area of 77 g/m$^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 1.

Example 1-6

Polypropylene fibers (2.2 dtex, 51 mm) and polyester fibers (1.7 dtex, 44 mm) were mixed at a weight ratio of 1:1 and subjected to carding to produce mixed fiber webs having a weight per unit area of 25 g/m$^2$, and thereafter, the webs were interlaced by continuously spraying high pressure water at 3 MPa and dried to produce a mixed fiber sheet. A nonwoven fabric having a weight per unit area of 12 g/m$^2$, which was made of side-by-side type composite thermal-bonding-based long fibers (fiber diameter of 30 μm) constituted with polyester and polyethylene was integrally laminated with the mixed fiber sheet by needle punching, and further the resulting product was subjected to frictionally charging treatment to obtain an electret laminate sheet.

A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.1 was sprayed to the side of the nonwoven fabric made of thermal-bonding-based long fibers of the obtained electret laminate sheet in such a manner that the weight per unit area was 220 g/m$^2$. Further, a thermally bonded nonwoven fabric having a weight per unit area of 77 g/m$^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 1.

Example 1-7

Polypropylene fibers (2.2 dtex, 51 mm) and polyester fibers (1.7 dtex, 44 mm) were mixed at a weight ratio of 1:1 and subjected to carding to produce mixed fiber webs having a weight per unit area of 25 g/m$^2$, and thereafter, the webs were interlaced by continuously spraying high pressure water at 3 MPa and dried to produce a mixed fiber sheet. A nonwoven fabric having a weight per unit area of 35 g/m$^2$, which was made of core-sheath type composite thermal-bonding-based long fibers (fiber diameter of 30 μm) constituted with polyester (core)/polyethylene (sheath) was integrally laminated with the mixed fiber sheet by needle punching, and further the resulting product was subjected to frictionally charging treatment to obtain an electret laminate sheet.

A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.1 was sprayed to the side of the nonwoven fabric made of thermal-bonding-based long fibers of the obtained electret laminate sheet in such a manner that the weight per unit area was 220 g/m$^2$. Further, a thermally bonded nonwoven fabric having a weight per unit area of 77 g/m$^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 1.

Example 1-8

Polypropylene fibers (2.2 dtex, 51 mm) and polyester fibers (1.7 dtex, 44 mm) were mixed at a weight ratio of 1:1 and subjected to carding to produce mixed fiber webs having a weight per unit area of 25 g/m$^2$, and thereafter, the webs were interlaced by continuously spraying high pressure water at 3 MPa and dried to produce a mixed fiber sheet. A nonwoven fabric having a weight per unit area of 12 g/m$^2$, which was made of core-sheath type composite thermal-bonding-based long fibers (fiber diameter of 30 μm) constituted with polyester (core)/polyethylene (sheath) was integrally laminated with the mixed fiber sheet by needle punching, and further the resulting product was subjected to frictionally charging treatment to obtain an electret laminate sheet.

A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.1 was sprayed to the side of the nonwoven fabric made of thermal-bonding-based long fibers of the obtained electret laminate sheet in such a manner that the weight per unit area was 440 g/m$^2$. Further, a thermally bonded nonwoven fabric having a weight per unit area of 77 g/m$^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 1.

Comparative Example 1-1

Polypropylene fibers (2.2 dtex, 51 mm) and polyester fibers (1.7 dtex, 44 mm) were mixed at a weight ratio of 1:1 and subjected to carding to produce mixed fiber webs having a weight per unit area of 25 g/m$^2$, and thereafter, the webs were interlaced by continuously spraying high pressure water at 3 MPa and dried to produce a mixed fiber sheet. This mixed fiber sheet was subjected to needle punching to cause friction among fibers so as to perform an electret treatment.

A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.1 was sprayed to the obtained electret nonwoven fabric in such a manner that the weight per unit area was 220 g/m$^2$. Further, a thermally bonded nonwoven fabric having a weight per unit area of 77 g/m$^2$ was superposed thereon as a base material layer, and a heat treatment at 140° C. was performed to make a sheet.

This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 2.

Comparative Example 1-2

Polypropylene fibers (2.2 dtex, 51 mm) and polyester fibers (1.7 dtex, 44 mm) were mixed at a weight ratio of 1:1 and subjected to carding to produce mixed fiber webs having a weight per unit area of 25 g/m$^2$, and thereafter, the webs were interlaced by continuously spraying high pressure water at 3 MPa and dried to produce a mixed fiber sheet. This mixed fiber sheet was subjected to needle punching to cause friction among fibers so as to perform an electret treatment.

A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.2 was sprayed to the obtained electret nonwoven fabric in such a manner that the weight per unit area was 240 g/m$^2$. Further, a thermally bonded nonwoven fabric having a weight per unit area of 77 g/m$^2$ was superposed thereon as a base material layer, and a heat treatment at 140° C. was performed to make a sheet.

This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 2.

Comparative Example 1-3

Polypropylene fibers (2.2 dtex, 51 mm) and polyester fibers (1.7 dtex, 44 mm) were mixed at a weight ratio of 1:1 and subjected to carding to produce mixed fiber webs having a weight per unit area of 25 g/m$^2$, and thereafter, the webs were interlaced by continuously spraying high pressure water at 3 MPa and dried to produce a mixed fiber sheet. A low melting point polyester having a weight per unit area of 12 g/m$^2$ (fiber diameter of 30 μm) was integrally laminated with the mixed fiber sheet by needle punching, and further the resulting product was subjected to frictionally charging treatment to obtain an electret laminate sheet.

A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.1 was sprayed to the side of the nonwoven fabric made of thermal-bonding-based long fibers of the obtained electret laminate sheet in such a manner that the weight per unit area was 220 g/m$^2$. Further, a thermally bonded nonwoven fabric having a weight per unit area of 77 g/m$^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 2.

Example 2-1

A melt-blown nonwoven fabric (weight per unit area 20 g/m$^2$, fiber diameter 6.5 μm) made of polypropylene and a nonwoven fabric (weight per unit area 12 g/m$^2$, fiber diameter 30 μm) made of thermal-bonding-based long fibers and constituted with polyester (core)/polyethylene (sheath) were integrally laminated with use of an adhesive resin. A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained laminate sheet in such a manner that the weight per unit area was 210 g/m$^2$. Further, a thermally bonded nonwoven fabric having a weight per unit area of 77 g/m$^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 3.

Example 2-2

A melt-blown nonwoven fabric (weight per unit area 20 g/m$^2$, fiber diameter 6.5 μm) made of polypropylene and a nonwoven fabric (weight per unit area 12 g/m$^2$, fiber diameter 30 μm) made of thermal-bonding-based long fibers and constituted with polyester (core)/polyethylene (sheath) were integrally laminated with use of an adhesive resin. A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained laminate sheet in such a manner that the weight per unit area was 315 g/m$^2$. Further, a thermally bonded nonwoven fabric having a weight per unit area of 77 g/m$^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 3.

Example 2-3

A melt-blown nonwoven fabric (weight per unit area 20 g/m$^2$, fiber diameter 6.5 μm) made of polypropylene and a nonwoven fabric (weight per unit area 12 g/m$^2$, fiber diameter 30 μm) made of thermal-bonding-based long fibers and constituted with polyester (core)/polyethylene (sheath) were integrally laminated by nipping with two heat rolls. A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained laminate sheet in such a manner that the weight per unit area was 315 g/m$^2$. Further, a thermally bonded nonwoven fabric having a weight per unit area of 77 g/m$^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 3.

Example 2-4

A melt-blown nonwoven fabric (weight per unit area 20 $g/m^2$, fiber diameter 6.5 μm) made of polypropylene and a nonwoven fabric (weight per unit area 20 $g/m^2$, fiber diameter 30 μm) made of thermal-bonding-based long fibers and constituted with polyester (core)/polyethylene (sheath) were integrally laminated by nipping with two heat rolls. A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained laminate sheet in such a manner that the weight per unit area was 315 $g/m^2$. Further, a thermally bonded nonwoven fabric having a weight per unit area of 77 $g/m^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 3.

Example 2-5

A melt-blown nonwoven fabric (weight per unit area 20 $g/m^2$, fiber diameter 6.5 μm) made of polypropylene and a nonwoven fabric (weight per unit area 12 $g/m^2$, fiber diameter 30 μm) made of thermal-bonding-based long fibers and constituted with polyester (core)/polyethylene (sheath) were integrally laminated by needle punching. A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained laminate sheet in such a manner that the weight per unit area was 315 $g/m^2$. Further, a thermally bonded nonwoven fabric having a weight per unit area of 77 $g/m^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 3.

Example 2-6

A melt-blown nonwoven fabric (weight per unit area 20 $g/m^2$, fiber diameter 6.5 μm) made of polypropylene and a nonwoven fabric (weight per unit area 20 $g/m^2$, fiber diameter 30 μm) made of thermal-bonding-based long fibers and constituted with polyester (core)/polyethylene (sheath) were integrally laminated by nipping with two heat rolls. A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained laminate sheet in such a manner that the weight per unit area was 368 $g/m^2$. Further, a thermally bonded nonwoven fabric having a weight per unit area of 77 $g/m^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 3.

Example 2-7

A melt-blown nonwoven fabric (weight per unit area 20 $g/m^2$, fiber diameter 6.5 μm) made of polypropylene and a nonwoven fabric (weight per unit area 20 $g/m^2$, fiber diameter 30 μm) made of thermal-bonding-based long fibers and constituted with polyester (core)/polyethylene (sheath) were integrally laminated by nipping with two heat rolls. A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained laminate sheet in such a manner that the weight per unit area was 105 $g/m^2$. Further, a thermally bonded nonwoven fabric having a weight per unit area of 77 $g/m^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 3.

Example 2-8

A melt-blown nonwoven fabric (weight per unit area 30 $g/m^2$, fiber diameter 6.5 μm) made of polypropylene and a nonwoven fabric (weight per unit area 20 $g/m^2$, fiber diameter 30 μm) made of thermal-bonding-based long fibers and constituted with polyester (core)/polyethylene (sheath) were integrally laminated by nipping with two heat rolls. A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained laminate sheet in such a manner that the weight per unit area was 105 $g/m^2$. Further, a thermally bonded nonwoven fabric having a weight per unit area of 77 $g/m^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 3.

Comparative Example 2-1

A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to a melt-blown nonwoven fabric (weight per unit area 20 g/m$^2$, fiber diameter 6.5 μm) made of polypropylene in such a manner that the weight per unit area was 315 g/m$^2$. Further, a thermally bonded nonwoven fabric having a weight per unit area of 77 g/m$^2$ was superposed thereon, and a heat treatment at 120° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 4.

Comparative Example 2-2

A melt-blown nonwoven fabric (weight per unit area 20 g/m$^2$, fiber diameter 6.5 μm) made of polypropylene and a nonwoven fabric (weight per unit area 50 g/m$^2$, fiber diameter 30 μm) made of thermal-bonding-based long fibers and constituted with polyester (core)/polyethylene (sheath) were integrally laminated by nipping with two heat rolls. A mixed powder containing coconut husk activated carbon having an average particle diameter of 550 μm and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained laminate sheet in such a manner that the weight per unit area was 315 g/m$^2$. Further, a thermally bonded nonwoven fabric having a weight per unit area of 77 g/m$^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 4.

Comparative Example 2-3

A melt-blown nonwoven fabric (weight per unit area 20 g/m$^2$, fiber diameter 6.5 μm) made of polypropylene and a nonwoven fabric (weight per unit area 50 g/m$^2$, fiber diameter 30 μm) made of thermal-bonding-based long fibers and constituted with polyester (core)/polyethylene (sheath) were integrally laminated by nipping with two heat rolls. A mixed powder containing coconut husk activated carbon having an average particle diameter of 550 μmin and FLO-BEADS EA 209 manufactured by Sumitomo Seika Chemicals Co., Ltd. as a thermoplastic powder resin at a weight ratio of 1:0.05 was sprayed to the side of the nonwoven fabric made of thermal-bonding-based long fibers of the obtained laminate sheet in such a manner that the weight per unit area was 630 g/m$^2$. Further, a thermally bonded nonwoven fabric having a weight per unit area of 77 g/m$^2$ was superposed thereon, and a heat treatment at 140° C. was performed to make a sheet. This filtering medium was processed into a pleat shape having a projection height of 28 mm and a pitch of 6 mm by a pleating machine to produce a filter having an outer dimension of 200 mm×200 mm.

The results of various measurements for the obtained filtering medium and filter are shown in Table 4.

TABLE 1

| | | | Example 1-1 | Example 1-2 | Example 1-3 | Example 1-4 |
|---|---|---|---|---|---|---|
| Laminate sheet | Needle-punched electret nonwoven fabric | Weight per unit area (g/m$^2$) | 25 | 25 | 15 | 45 |
| | thermal-bonding nonwoven fabric | Type | long fiber | long fiber | long fiber | long fiber |
| | | Weight per unit area (g/m$^2$) | 12 | 12 | 12 | 20 |
| | | Component | (core)PES (sheath)PE | (core)PES (sheath)PE | (core)PES (sheath)PE | (core)PES (sheath)PE |
| Adsorbing layer | | Weight of adsorbent (g/m$^2$) | 200 | 200 | 300 | 300 |
| | | Ratio of adhesive (%) | 10 | 5 | 5 | 5 |
| | | Weight of adhesive (g/m$^2$) | 20 | 10 | 15 | 15 |
| Base material layer | | Weight per unit area (g/m$^2$) | 77 | 77 | 77 | 77 |
| Properties of sheet | | Weight per unit area (g/m$^2$) | 334 | 324 | 419 | 457 |
| | | Pressure loss (Pa) | 36 | 33 | 35 | 37 |
| | | Collection efficiency for 0.3 μm particles (%) | 33 | 34 | 26 | 27 |
| | | Adhesive strength (MD direction) (N/50 mm) | 4.2 | 2.4 | 2.5 | 3.1 |
| | | Rigidity (MD direction) (g) | 4.3 | 2.2 | 2.6 | 3.0 |
| | | Toluene removal efficiency (%) | 52 | 61 | 75 | 74 |
| Properties of filter | | Pressure loss (Pa) | 108 | 93 | 132 | 140 |
| | | ASHRAE dust-holding capacity (g/filter) | 365 | 388 | 382 | 354 |

| | | | Example 1-5 | Example 1-6 | Example 1-7 | Example 1-8 |
|---|---|---|---|---|---|---|
| Laminate sheet | Needle-punched electret nonwoven fabric | Weight per unit area (g/m$^2$) | 45 | 25 | 25 | 25 |
| | thermal-bonding nonwoven fabric | Type | long fiber | long fiber | long fiber | long fiber |
| | | Weight per unit area (g/m$^2$) | 12 | 12 | 35 | 12 |
| | | Component | (core)PES (sheath)PE | side-by-side PES/PE | (core)PES (sheath)PE | (core)PES (sheath)PE |
| Adsorbing layer | | Weight of adsorbent (g/m$^2$) | 300 | 200 | 200 | 400 |
| | | Ratio of adhesive (%) | 5 | 10 | 10 | 10 |
| | | Weight of adhesive (g/m$^2$) | 15 | 20 | 20 | 40 |

TABLE 1-continued

| | | | | | |
|---|---|---|---|---|---|
| Base material layer | Weight per unit area (g/m$^2$) | 77 | 77 | 77 | 77 |
| Properties of sheet | Weight per unit area (g/m$^2$) | 449 | 334 | 357 | 554 |
| | Pressure loss (Pa) | 39 | 34 | 42 | 44 |
| | Collection efficiency for 0.3 μm particles (%) | 48 | 33 | 34 | 33 |
| | Adhesive strength (MD direction) (N/50 mm) | 3.2 | 2.6 | 3.8 | 3.2 |
| | Rigidity (MD direction) (g) | 3.1 | 2.8 | 3.4 | 2.2 |
| | Toluene removal efficiency (%) | 74 | 62 | 61 | 82 |
| Properties of filter | Pressure loss (Pa) | 141 | 134 | 135 | 155 |
| | ASHRAE dust-holding capacity (g/filter) | 392 | 343 | 331 | 284 |

TABLE 2

| | | | Comparative Example 1-2 | Comparative Example 1-2 | Comparative Example 1-3 |
|---|---|---|---|---|---|
| Laminate sheet | Needle-punched electret nonwoven fabric | Weight per unit area (g/m$^2$) | 25 | 25 | 25 |
| | thermal-bonding nonwoven fabric | Type | long fiber | long fiber | long fiber |
| | | Weight per unit area (g/m$^2$) | 0 | 0 | 12 |
| | | Component | — | — | low melting point PES |
| Adsorbing layer | | Weight of adsorbent (g/m$^2$) | 200 | 200 | 200 |
| | | Ratio of adhesive (%) | 10 | 20 | 10 |
| | | Weight of adhesive (g/m$^2$) | 20 | 40 | 20 |
| Base material layer | | Weight per unit area (g/m$^2$) | 77 | 77 | 77 |
| Properties of sheet | | Weight per unit area (g/m$^2$) | 322 | 342 | 334 |
| | | Pressure loss (Pa) | 35 | 39 | 36 |
| | | Collection efficiency for 0.3 μm particles (%) | 32 | 27 | 14 |
| | | Adhesive strength (MD direction) (N/50 mm) | 1.2 | 3.9 | 3.3 |
| | | Rigidity (MD direction) (g) | 1.1 | 3.2 | 2.4 |
| | | Toluene removal efficiency (%) | 48 | 41 | 60 |
| Properties of filter | | Pressure loss (Pa) | 138 | 145 | 162 |
| | | ASHRAE dust-holding capacity (g/filter) | 282 | 265 | 277 |

TABLE 3

| | | | Example 2-1 | Example 2-2 | Example 2-3 | Example 2-4 |
|---|---|---|---|---|---|---|
| Laminate sheet | Melt-blown nonwoven fabric | Weight per unit area (g/m$^2$) | 20 | 20 | 20 | 20 |
| | | Fiber diameter (μm) | 6.5 | 6.5 | 6.5 | 6.5 |
| | Long fiber nonwoven fabric | Weight per unit area (g/m$^2$) | 12 | 12 | 12 | 20 |
| | Adsorbing layer | Weight of adsorbent (g/m$^2$) | 200 | 300 | 300 | 300 |
| | | Ratio of adhesive (%) | 5 | 5 | 5 | 5 |
| | | Weight of adhesive (g/m$^2$) | 10 | 15 | 15 | 15 |
| | Base material layer | Weight per unit area (g/m$^2$) | 77 | 77 | 77 | 77 |
| | Properties of sheet | Weight per unit area (g/m$^2$) | 319 | 424 | 424 | 432 |
| | | Pressure loss (Pa) | 46 | 53 | 52 | 55 |
| | | Collection efficiency for 0.3 μm particles (%) | 33 | 34 | 35 | 36 |
| | | Adhesive strength (MD direction) (N/50 mm) | 2.4 | 2.4 | 2.4 | 3.5 |
| | | Rigidity (MD direction) (g) | 2.1 | 2.2 | 2.3 | 3.4 |
| | | Toluene removal efficiency (%) | 56 | 70 | 72 | 75 |
| | Properties of filter | Pressure loss (Pa) | 129 | 153 | 151 | 161 |
| | | ASHRAE dust-holding capacity (g/filter) | 290 | 244 | 256 | 245 |
| | | | Example 2-5 | Example 2-6 | Example 2-7 | Example 2-8 |
| Laminate sheet | Melt-blown nonwoven fabric | Weight per unit area (g/m$^2$) | 20 | 20 | 20 | 30 |
| | | Fiber diameter (μm) | 6.5 | 6.5 | 6.5 | 6.5 |
| | Long fiber nonwoven fabric | Weight per unit area (g/m$^2$) | 12 | 12 | 12 | 12 |

TABLE 3-continued

| | | | | | |
|---|---|---|---|---|---|
| Adsorbing layer | Weight of adsorbent (g/m$^2$) | 300 | 350 | 100 | 100 |
| | Ratio of adhesive (%) | 5 | 5 | 5 | 5 |
| | Weight of adhesive (g/m$^2$) | 15 | 18 | 5 | 5 |
| Base material layer | Weight per unit area (g/m$^2$) | 77 | 77 | 77 | 77 |
| Properties of sheet | Weight per unit area (g/m$^2$) | 424 | 477 | 214 | 224 |
| | Pressure loss (Pa) | 49 | 56 | 38 | 63 |
| | Collection efficiency for 0.3 μm particles (%) | 30 | 33 | 33 | 57 |
| | Adhesive strength (MD direction) (N/50 mm) | 2.6 | 3.1 | 2.2 | 2.1 |
| | Rigidity (MD direction) (g) | 2.8 | 3.2 | 1.9 | 1.7 |
| | Toluene removal efficiency (%) | 73 | 83 | 51 | 52 |
| Properties of filter | Pressure loss (Pa) | 143 | 157 | 123 | 148 |
| | ASHRAE dust-holding capacity (g/filter) | 284 | 254 | 304 | 256 |

TABLE 4

| | | | Comparative Example 2-1 | Comparative Example 2-2 | Comparative Example 2-3 |
|---|---|---|---|---|---|
| Laminate sheet | Melt-blown nonwoven fabric | Weight per unit area (g/m$^2$) | 20 | 20 | 20 |
| | | Fiber diameter (μm) | 6.5 | 6.5 | 6.5 |
| | Long fiber nonwoven fabric | Weight per unit area (g/m$^2$) | 0 | 50 | 12 |
| | Adsorbing layer | Weight of adsorbent (g/m$^2$) | 300 | 300 | 600 |
| | | Ratio of adhesive (%) | 5 | 5 | 5 |
| | | Weight of adhesive (g/m$^2$) | 15 | 15 | 30 |
| | Base material layer | Weight per unit area (g/m$^2$) | 77 | 77 | 77 |
| | Properties of sheet | Weight per unit area (g/m$^2$) | 412 | 462 | 739 |
| | | Pressure loss (Pa) | 48 | 55 | 60 |
| | | Collection efficiency for 0.3 μm particles (%) | 32 | 33 | 36 |
| | | Adhesive strength (MD direction) (N/50 mm) | 1.1 | 2.4 | 2.2 |
| | | Rigidity (MD direction) (g) | 0.8 | 2.8 | 2.1 |
| | | Toluene removal efficiency (%) | 70 | 71 | 99 |
| | Properties of filter | Pressure loss (Pa) | 189 | 182 | 181 |
| | | ASHRAE dust-holding capacity (g/filter) | 154 | 160 | 85 |

INDUSTRIAL APPLICABILITY

The present invention is a filtering medium for deodorizing filter excellent in pressure loss and dust-holding capacity. Accordingly, the filtering medium is usable for a long period of time and significantly contributes to industrial fields.

The invention claimed is:

1. A filtering medium for deodorizing filter having a laminated structure formed by sandwiching an adsorbing layer containing an adsorbent and an adhesive between base material layers, wherein at least one layer of the base material layers is a laminate sheet obtained by integrally laminating a nonwoven fabric made of thermal-bonding-based long fibers and a nonwoven fabric made of polyolefin-based fibers and polyester-based fibers by needle punching; and the adsorbing layer and the nonwoven fabric made of thermal-bonding-based long fibers of the laminate sheet are laminated so as to be adjacent to each other and thermally bonded to each other, wherein the nonwoven fabric made of thermal-bonding-based long fibers is a nonwoven fabric made of composite thermal-bonding-based long fibers having a core-sheath structure.

2. A filtering medium for deodorizing filter having a laminate structure formed by sandwiching 10 to 450 g/m$^2$ of an adsorbing layer containing an adsorbent and an adhesive between base material layers, wherein at least one layer of the base material layers is a laminate sheet obtained by laminating a nonwoven fabric made of thermal-bonding-based long fibers having a weight per unit area of 5 to 40 g/m$^2$ and a melt-blown nonwoven fabric; and the adsorbing layer and the nonwoven fabric made of thermal-bonding-based long fibers of the laminate sheet are laminated so as to be adjacent to each other and thermally bonded to each other, wherein the nonwoven fabric made of thermal-bonding-based long fibers is a nonwoven fabric made of composite thermal-bonding-based long fibers having a core-sheath structure.

3. The filtering medium for deodorizing filter according to claim 1, wherein the content of the adhesive is 1 to 40 wt % based on the content of the adsorbent in the adsorbing layer.

4. The filtering medium for deodorizing filter according to claim 2, wherein the content of the adhesive is 1 to 40 wt % based on the content of the adsorbent in the adsorbing layer.

* * * * *